US012678616B2

(12) United States Patent
Li et al.

(10) Patent No.: US 12,678,616 B2
(45) Date of Patent: Jul. 14, 2026

(54) FLEXIBLE ELECTRODE FOR BRAIN AND METHOD FOR MANUFACTURING SAME

(71) Applicant: CENTER FOR EXCELLENCE IN BRAIN SCIENCE AND INTELLIGENCE TECHNOLOGY, CHINESE ACADEMY OF SCIENCES, Shanghai (CN)

(72) Inventors: Xue Li, Shanghai (CN); Zhengtuo Zhao, Shanghai (CN); Xiaocheng Li, Shanghai (CN); Chengyao Wang, Shanghai (CN)

(73) Assignee: CENTER FOR EXCELLENCE IN BRAIN SCIENCE AND INTELLIGENCE TECHNOLOGY, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 18/983,713

(22) Filed: Dec. 17, 2024

(65) Prior Publication Data

US 2025/0114595 A1 Apr. 10, 2025

Related U.S. Application Data

(63) Continuation of application No. PCT/CN2022/102320, filed on Jun. 29, 2022.

(51) Int. Cl.
*A61N 1/05* (2006.01)

(52) U.S. Cl.
CPC ......... *A61N 1/0534* (2013.01); *A61N 1/0531* (2013.01); *A61N 1/0539* (2013.01)

(58) Field of Classification Search
CPC ... A61N 1/0534; A61N 1/0531; A61N 1/0539
See application file for complete search history.

(56) References Cited

U.S. PATENT DOCUMENTS

2002/0045832 A1 4/2002 Giller et al.
2003/0125786 A1 7/2003 Gliner et al.
(Continued)

FOREIGN PATENT DOCUMENTS

CN 108751116 A 11/2018
CN 108903916 A 11/2018
(Continued)

OTHER PUBLICATIONS

International Search Report and Written Opinion from International Application No. PCT/CN2022/102320 mailed Dec. 29, 2022.
(Continued)

*Primary Examiner* — Unsu Jung
*Assistant Examiner* — Philip C Edwards
(74) *Attorney, Agent, or Firm* — GREENBERG TRAURIG, LLP

(57) ABSTRACT

The present disclosure relates to a flexible electrode for a brain and a method for manufacturing the same. Provided is a flexible electrode for the brain, which comprises a cortical attachment portion that can be implanted into the brain, and one or more deep implantation portions, the cortical attachment portion having a sheet-like structure capable of covering and being flattened to fit against at least a portion of a cerebral cortex after implantation, and the deep implantation portions being configured to be implanted into a deep region of the brain and bent relative to the cortical attachment portion after implantation, wherein the deep implantation portions and the cortical attachment portion each comprise one or more electrode sites, each of the electrode sites being electrically coupled to one of wires in the wire layer and being in contact with the brain after the flexible electrode is implanted into the brain.

28 Claims, 9 Drawing Sheets

(56) References Cited

U.S. PATENT DOCUMENTS

| 2005/0070971 | A1 |  | 3/2005 | Fowler et al. |
| 2010/0130844 | A1 |  | 5/2010 | Williams et al. |
| 2012/0271316 | A1 |  | 10/2012 | Pianca et al. |
| 2014/0222103 | A1 |  | 8/2014 | Lauritzen et al. |
| 2017/0014622 | A1 |  | 1/2017 | Bozung et al. |
| 2021/0170175 | A1 | * | 6/2021 | Schobben ............ A61N 1/0526 |
| 2023/0045240 | A1 | * | 2/2023 | Park ........................ A61N 1/36 |

FOREIGN PATENT DOCUMENTS

| CN |  | 112022154 | A | 12/2020 |
| CN |  | 112450939 | A | 3/2021 |
| WO |  | 2022/006317 | A1 | 1/2022 |

OTHER PUBLICATIONS

The Third Examination Opinion Notification from Chinese Patent Application No. 202210689958.0 dated Feb. 17, 2025.

* cited by examiner

200 manufacture, on a substrate, a first insulating layer, a wire layer, and a second insulating layer, wherein a via hole is manufactured by patterning at a position in at least one of the first insulating layer or the second insulating layer that corresponds to an electrode site    S41 separate the flexible electrode from the substrate    S42

400

FLEXIBLE ELECTRODE FOR BRAIN AND METHOD FOR MANUFACTURING SAME

CROSS-REFERENCE TO RELATED APPLICATIONS

This application is based on and claims the priority to the Chinese application No. 202210689958.0 filed on Jun. 17, 2022, the subject matter of which is hereby incorporated by reference in its entirety.

TECHNICAL FIELD

The present disclosure relates to the technical field of life science, and more specifically, to a flexible electrode for a brain and a method for manufacturing same.

BACKGROUND

A brain is a center of a nervous system, affecting various functions of survival and life, such as language, movement and memory.

At present, in medical or research occasions, such as treatment of an organic lesion of the brain, enabling a paralyzed or limb-deficient patient to independently interact with the outside, exploration of a neuronal mechanism for regulation of human brain and limbs, there is a need to perform positioning, recording and functional electrical stimulation on electric signals of the brain.

SUMMARY

A brief summary of the present disclosure is presented hereinafter to provide a basic understanding of some aspects of the present disclosure. However, it should be understood that this summary is not an exhaustive summary of the present disclosure. It is not intended to determine key or critical elements of the present disclosure or to limit the scope of the present disclosure. Its purpose is only to present certain concepts of the present disclosure in a simplified form as a prelude to the detailed description to be presented later.

According to a first aspect of the present disclosure, there is provided a flexible electrode for a brain, comprising a cortical attachment portion capable of being implanted into the brain and one or more deep implantation portions, the cortical attachment portion having a sheet-like structure capable of covering and being flattened to fit against at least a portion of a cerebral cortex after the implantation, the deep implantation portion being configured to be implanted into a deep region of the brain and bent relative to the cortical attachment portion after the implantation, wherein, the flexible electrode comprises a first insulating layer, a second insulating layer, and a wire layer located between the first insulating layer and the second insulating layer; and the deep implantation portion and the cortical attachment portion each comprise one or more electrode sites, each of which is electrically coupled to one of wires in the wire layer and in contact with the brain after the flexible electrode is implanted into the brain, to acquire, from the brain, an electrical signal and transmit the acquired electrical signal by the wire, or apply, to the brain, an electrical signal received by the wire.

According to a second aspect of the present disclosure, there is provided a method for manufacturing a flexible electrode for a brain, the flexible electrode being the flexible electrode according to the first aspect of the present disclosure, the method comprising: manufacturing, on a substrate, the first insulating layer, the wire layer, the second insulating layer, and the electrode site; and separating the flexible electrode from the substrate, wherein a via hole is manufactured by patterning, at a position of at least one of the first insulating layer or the second insulating layer that corresponds to the electrode site.

Other features of the present disclosure and advantages thereof will become more apparent by the following detailed description of exemplary embodiments thereof, which proceeds with reference to the accompanying drawings.

BRIEF DESCRIPTION OF THE DRAWINGS

The accompanying drawings, which constitute a part of this specification, illustrate embodiments of the present disclosure and together with the description, serve to explain the principles of the present disclosure.

The present disclosure may be more clearly understood from the following detailed description by referring to the accompanying drawings, in which.

DETAILED DESCRIPTION

Figure 1:
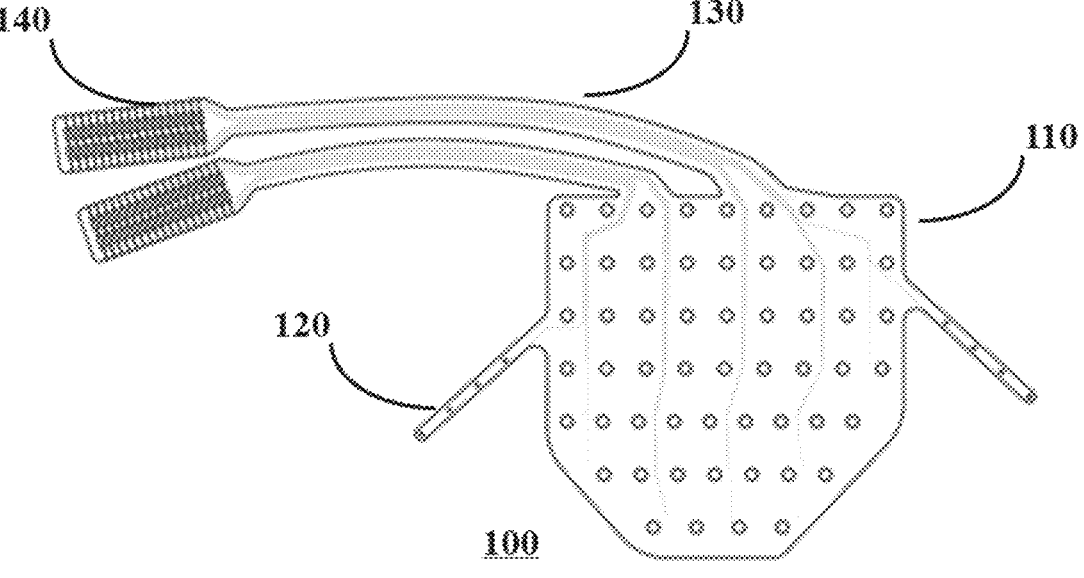
FIG. 1 illustrates a schematic view of at least a portion of a flexible electrode for a brain according to an embodiment of the present disclosure.

The following detailed description is made with reference to the accompanying drawings and is provided to aid in a comprehensive understanding of various exemplary embodiments of the present disclosure. The following description includes various details to aid understanding, but these details are regarded as examples only and are not intended to limit the present disclosure, which is defined by the appended claims and their equivalents. The words and phrases used in the following description are intended only to provide a clear and consistent understanding of the present disclosure. In addition, descriptions of well-known structures, functions, and configurations may be omitted for clarity and conciseness. Those of ordinary skill in the art will recognize that various changes and modifications of the examples described herein can be made without departing from the spirit and scope of the present disclosure.

The following description of at least one exemplary embodiment is merely illustrative in nature and is in no way construed as any limitation on this disclosure and its application or use. That is, the structures and methods herein are shown in exemplary ways to illustrate different embodiments of the structures and methods of the present disclosure. Those skilled in the art will understand, however, that they are merely illustrative of exemplary ways in which the present disclosure may be implemented, rather than exhaustive ways. Furthermore, the accompanying drawings are not necessarily drawn to scale, and some features may be enlarged to show details of specific components.

Techniques, methods, and devices known to one of ordinary skill in the related art may not be discussed in detail but are intended to be part of the granted specification where appropriate.

In all examples shown and discussed herein, any specific value should be construed as exemplary only and not as limiting. Thus, other examples of the exemplary embodiments may have different values.

At present, a common electrode for a brain is a cerebral cortex electrode, but the cerebral cortex electrode will have defects in hardness or thickness or the like due to the material and electrode structure selected therein, and ideal signal recording and stimulation cannot be implemented in aspects of shape and channel number.

On the other hand, so far, there still lacks deep research on whether an individual neuron or a nervous activity on a larger neural network scale had a greater impact on understanding and restoring neural functions. Because individual neuronal spikes and electrocorticography (ECOG) reflect different aspects of the nerve functions, a relationship between these measurement signals is gradually gaining research attention.

In terms of synchronous recording of surface and deep neural signals, at present, most researches adopt independent processing and separate implantation for a surface planar electrode and a deep penetrating electrode, but the separate implantation not only affects relative position accuracy between the two electrodes, but also requires connection with the outside through their respective interfaces, resulting in certain difficulty in implantation and connection of the electrode.

There are few devices that can simultaneously monitor nervous activity on both surface and deep spatial scales, while this is crucial for understanding relationships of individual neurons with a large-scale brain network as well as with behaviors. Therefore, there is an urgent need to develop a neural recording function with cortical and deep dual modes while integrating a stimulation function, to provide a novel tool for neuroscience research.

FIG. 1 illustrates an exploded view of at least a portion of a flexible electrode 100 for a brain according to an embodiment of the present disclosure. As shown in FIG. 1, the flexible electrode 100 may comprise a cortical attachment portion 110 capable of being implanted into the brain and one or more deep implantation portions 120. The cortical attachment portion 110 may be in a sheet-like structure capable of covering and being flattened to fit into at least a portion of a cerebral cortex after the implantation. The deep implantation portion 120 may be configured to be implanted into a deep region of the brain, and due to good flexibility of the flexible electrode 100 itself, the deep implantation portion 120 may be bent relative to the cortical attachment portion after the implantation, thereby sensing and stimulating the deep region of the brain.

As shown in FIG. 1, the flexible electrode 100 may be manufactured in a planar structure. The deep implantation portion 120 may be located in the same plane as the cortical attachment portion 110 and at any desired angle with respect to an edge of the cortical attachment portion 110.

In the embodiment according to the present disclosure, the deep implantation portion 120 of the flexible electrode 100 may extend from the cortical attachment portion 110 and have a mounting hole (not shown). An electrode implantation device (e.g., a tungsten wire, etc.) is, by means of the mounting hole, attached to the deep implantation portion 120 to guide the implantation of the deep implantation portion 120 at a desired position and angle. Due to the good flexibility of the flexible electrode 100 itself, the deep implantation portion 120 can be bent for implantation at any desired position and angle.

In the embodiment according to the present disclosure, the flexible electrode 100 may further comprise a backend portion 140 extending from the cortical attachment portion 110, the backend portion 140 being connected to the cortical attachment portion 110 through a connection portion 130 and usable for joining the flexible electrode 100 and a backend circuit for backend transfer. In the embodiment shown in FIG. 1, the flexible electrode 100 includes two backend portions 140 and two connection portions 130 each extending from the cortical attachment portion 110 to one of the backend portions 140. However, it should be understood that the present disclosure is not so limited, but it may include one or more backend portions 140 and one or more corresponding connection portions 130 as needed, and each connection portion 130 may be connected to the one or more backend portions 140.

The flexible electrode 100 shown in FIG. 1 includes the irregularly shaped cortical attachment portion 110, the linear deep implantation portion 120, and the elongated connection portions 130 and the backend portions 140, but it should be understood that FIG. 1 shows only a non-limiting example, and the flexible electrode for the brain may have differently shaped and sized cortical attachment portion 110, deep implantation portion 120, connection portion 130, and backend portion 140 as needed.

Figure 2:
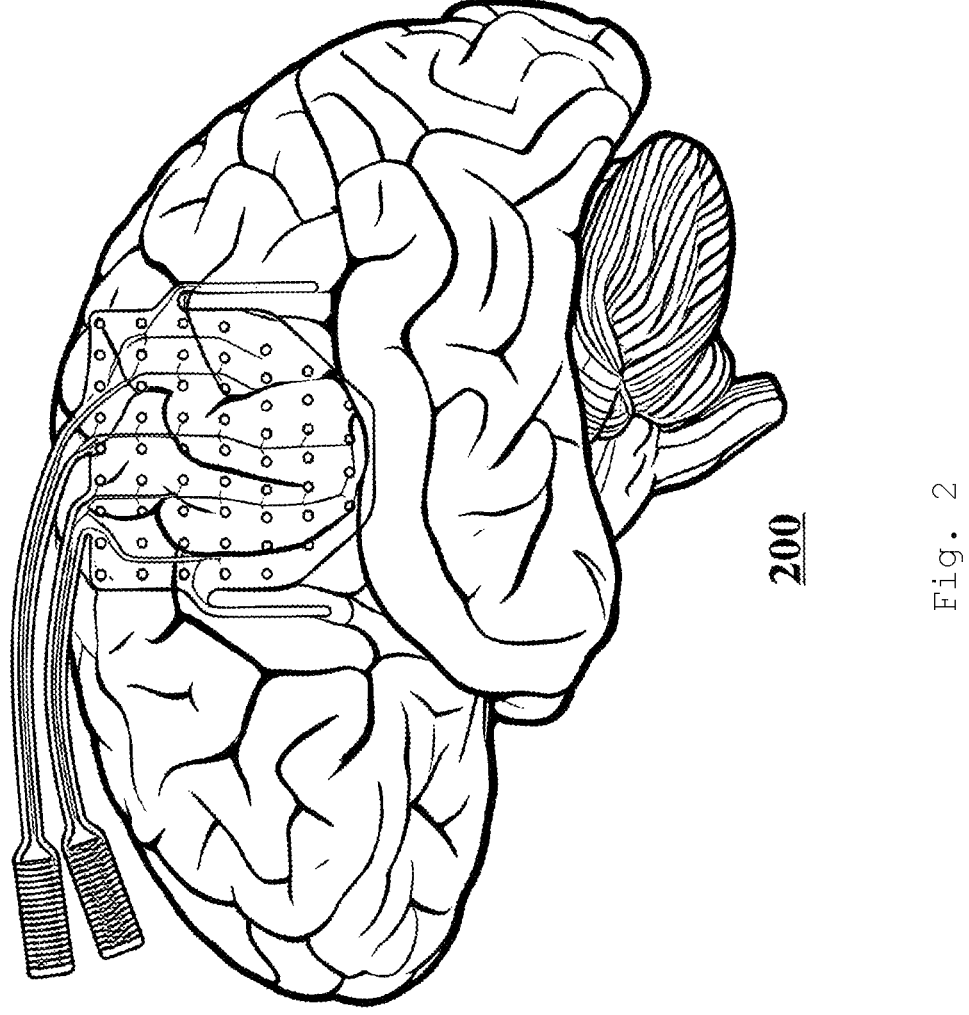
FIG. 2 illustrates a schematic view of an implantation position of a flexible electrode for a brain according to an embodiment of the present disclosure.

FIG. 2 illustrates a schematic view of an implantation position 200 of a flexible electrode for a brain according to an embodiment of the present disclosure. As shown in FIG. 2, the cortical attachment portion of the flexible electrode may be flattened to fit into the human cerebral cortex, to acquire an electrical signal of the cerebral cortex or apply electrical stimulation to the cerebral cortex. The deep implantation portion of the flexible electrode may be implanted into a deep region of the human brain and bent relative to the cortical attachment portion after the implantation, to acquire an electrical signal of the deep region of the brain or apply electrical stimulation to the deep region of the brain.

When the flexible electrode is implanted, it is possible to attach unfolded flexible electrodes one by one to the electrode implantation device (such as a tungsten wire of the electrode implantation device) by polyethylene glycol (PEG), and fix the tungsten wire by using the PEG. Then, the entire electrode system is fixed onto the electrode implantation device (such as a micromanipulator of the electrode implantation device) and moved above a targeted encephalic region. The cortical attachment portion and the deep implantation portion of the flexible electrode are implanted by using a support bracket with a micro-mechanical structure, the support bracket being capable of delivering, along a gap between a cerebrum and a skull, the flexible electrode into a position that is not easily accessible by craniotomy, such as a frontal lobe, while keeping the flexible electrode flattened and unfolded after delivered into the brain, with low trauma to the cerebrum. In other words, in the implantation of the flexible electrode using the support bracket (such as implantation of the electrode along the gap between the cerebrum and the skull), craniotomy may be avoided to protect a portion in the encephalic region that is prone to trauma, including an anterior frontal lobe, a posterior occipital lobe, an inferior temporal lobe, or a central cerebral great vessel.

Figure 3:
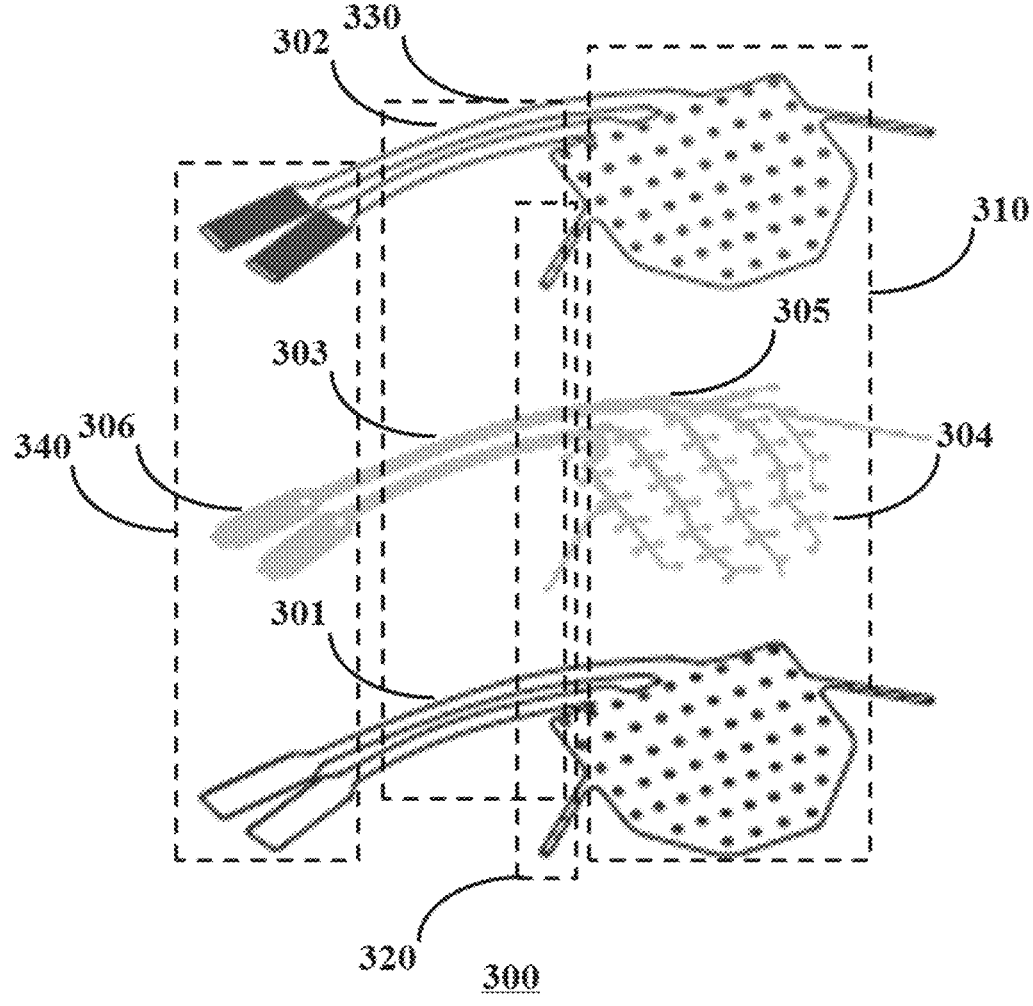
FIG. 3 illustrates an exploded view of at least a portion of a flexible electrode for a brain according to an embodiment of the present disclosure.

FIG. 3 illustrates an exploded view of at least a portion of a flexible electrode 300 for a brain according to an embodiment of the present disclosure. It can be clearly seen from FIG. 3 that, the flexible electrode is in a 300 multilayer structure, specifically including a bottom insulating layer 301, a top insulating layer 302, a wire layer 303, and the like. It should be understood that the layers of the flexible electrode 300 shown in FIG. 3 are merely non-limiting examples, and the flexible electrode in the present disclosure may include more other layers, such as an electrode site layer, a backend site layer, and a flexible separation layer.

The flexible electrode 300 may include the bottom insulating layer 301 and the top insulating layer 302. Specifically, as shown in FIG. 3, a cortical attachment portion 310, a deep implantation portion 320, a connection portion 330, and a backend portion 340 of the flexible electrode 300 may each include insulating layers 301 and 302. The insulating layer in the flexible electrode may refer to an outer surface layer of the electrode that functions as insulation. Since the insulating layer of the flexible electrode needs to be in contact with the cerebrum after the implantation, it is required that a material of the insulating layer has good biocompatibility while having good insulation. In the embodiment of the present disclosure, the material of the insulating layers 301 and 302 may include polyimide (PI), polydimethylsiloxane (PDMS), parylene, epoxy, polyamide imide (PAI), SU-8 photoresist, silica gel, silicone rubber, and the like. In the embodiment according to the present disclosure, in order to make the flexible electrode further have a biodegradable property, the material of the insulating layers 301 and 302 may further include polylactic acid, polylactic acid-glycolic acid copolymer, and the like. Furthermore, the insulating layers 301 and 302 are also a main portion in the flexible electrode 300 that provides strength. An excessively thin insulating layer will reduce strength of the electrode, an excessively thick insulating layer will reduce flexibility of the electrode, and implantation of the electrode including the excessively thick insulating layer will cause great damage to an organism. In the embodiment according to the present disclosure, the insulating layers 301 and 302 may have a thickness of 100 nm to 300 μm.

The flexible electrode 300 may further include one or more wires 305 spaced apart from each other in the wire layer 303 between the bottom insulating layer 301 and the top insulating layer 302. Specifically, as shown in FIG. 3, the cortical attachment portion 310, the deep implantation portion 320, the connection portion 330, and the backend portion 340 of the flexible electrode 300 may each include the wire layer 303. In the embodiment according to the present disclosure, each wire 305 in the wire layer 303 may, along the backend portion 340 and the connection portion 330, extend to the cortical attachment portion 310 and the deep implantation portion 320, and extend, in the cortical attachment portion 310 and the deep implantation portion 320, to electrode sites 304 located at the cortical attachment portion 310 and the deep implantation portion 320. In the embodiment according to the present disclosure, the flexible electrode 300 may include one or more wires 305 in the same wire layer 303, where each wire 305 may be electrically coupled to the electrode site 304 and to a backend site 306. In the embodiment according to the present disclosure, the wire layer 305 and the wires therein may have a thickness of 5 nm to 200 μm. The spacing between the wires may be as low as 10 nm, for example. A width of the wire and the spacing between the wires may be, for example, 10 nm to 500 μm, for example, preferably 300 nm to 3 μm. It should be understood that the size and the like of the wire are not limited to the range listed above, but may be changed according to design requirements.

In the embodiment according to the present disclosure, the wire 305 in the wire layer 303 may be in a film structure including a plurality of sub-layers stacked in a thickness direction. A material of these sub-layers may be a material that may enhance adhesion, ductility, conductivity, and the like of the wire. As a non-limiting example, the wire 305 may be a metal film including three stacked sub-layers, wherein a first sub-layer and a second sub-layer in contact with the insulating layers 301 and 302, respectively, are adhesion sub-layers, for which a metallic or non-metallic adhesive material such as titanium (Ti), titanium nitride (TiN), chromium (Cr), tantalum (Ta), or tantalum nitride (TaN) may be used, and a third sub-layer located between the first sub-layer and the second sub-layer is a conductive sub-layer, for which a material having good conductivity such as gold (Au), platinum (Pt), iridium (Ir), tungsten (W), platinum iridium alloy, titanium alloy, graphite, carbon nanotube, and PEDOT may be used. In the embodiment according to the present disclosure, in order to make the flexible electrode further have biodegradability, for the conductive sub-layer, a material such as magnesium (Mg), molybdenum (Mo), and alloy thereof may be further used. It should be understood that the wire 305 may be made of another metallic or non-metallic material with conductivity, or made of a polymer conductive material and composite conductive material. In the embodiment according to the present disclosure, the adhesion sub-layer may have a thickness of 1 nm to 50 nm.

As shown in FIG. 3, the electrode site 304 and the backend site 306 both can be located in the wire layer 303, and electrically coupled to a corresponding wire 305 in the wire layer 303. Specifically, the cortical attachment portion 310 and each deep implantation portion 320 of the flexible electrode 300 may comprise one or more electrode sites 304, each of which is electrically coupled to one of the wires in the wire layer 303, exposed to an outer surface of the flexible electrode 300 through a via hole in at least one of the bottom insulating layer 301 or the top insulating layer 302, and in contact with the brain after the implantation of the flexible electrode 300, to acquire, from the brain, an electrical signal and transmit the acquired electrical signal by the wire, or apply, to the brain, an electrical signal received by the wire. The one or more electrode sites 304 of the deep implantation portion 320 are usable for acquiring individual neuron spikes at different depths of a deep region of the brain and for applying electrical stimulation to the different depths. The one or more electrode sites 304 of the cortical attachment portion 310 are usable for acquiring, from the cerebral cortex, wider and shallower neuronal population activity, i.e., electrocorticography (ECOG), and for applying electrical stimulation to the cerebral cortex. Since each electrode site is coupled to its corresponding wire, when the flexible electrode 300 is taken as a stimulation electrode, each electrode site therein may apply same or different electrical signals, synchronously or asynchronously, at different positions of the deep region and/or surface of the brain; and when the flexible electrode 300 is taken as a sense electrode, these electrode sites can simultaneously finely acquire electrical signals at different positions of the deep region and/or surface of the brain. The spikes and ECOG signals have strong correlation, and the flexible electrode in the present disclosure can synchronously monitor nervous activity on surface and deep spatial scales, which is beneficial to understanding relationships of individual neurons with a large-scale brain network as well as with behaviors.

In the embodiment according to the present disclosure, the electrode sites may not be located in the wire layer, i.e. the flexible electrode may include a separate electrode site layer (not shown), e.g. a top electrode site layer or a bottom electrode site layer. The electrode site layer may be an outermost layer of the flexible electrode, such that the electrode sites are located on an outer surface of the flexible electrode, and each electrode site may be electrically coupled to a corresponding wire in the wire layer through a via hole in at least one of the top insulating layer or the bottom insulating layer. In this case, the electrode site in the electrode site layer may be in a film structure including a plurality of sub-layers stacked in a thickness direction. A material of an adhesion sub-layer close to the wire layer 303 in the plurality of sub-layers may be a material that may enhance adhesion between the electrode site and the wire, and the adhesion sub-layer may have a thickness of 1 nm to 50 nm. As a non-limiting example, the electrode site layer may be a metal film including two stacked sub-layers, wherein a first sub-layer close to the wire layer 303 is Ti, TiN, Cr, Ta, or TaN, and an exposed second sub-layer of the electrode site layer is Au. It should be understood that, similarly to the wire layer, the electrode site layer may also be made of another metallic or non-metallic material with conductivity, such as Pt, Ir, W, Mg, Mo, platinum iridium alloy, titanium alloy, graphite, carbon nanotube, PEDOT, etc.

In the present disclosure, each electrode site 304 may have a planar size in micrometers and a thickness in nanometers. In the embodiment according to the present disclosure, the electrode site 304 may be shaped as needed to various regular or irregular shapes, may be one or more in number, and may have a maximum side length or diameter of 1 µm to 500 µm, a spacing therebetween may be 10 µm to 10 mm, and a thickness thereof may be 5 nm to 200 µm. Moreover, in the embodiment according to the present disclosure, as shown in FIG. 3, the electrode site 304 of the deep implantation portion 320 may have a smaller size than the electrode site 304 of the cortical attachment portion 310, for example, the electrode site 304 of the deep implantation portion 320 may have a maximum side length or diameter of 1 µm to 2 mm, and the electrode site 304 of the cortical attachment portion 310 may have a maximum side length or diameter of 1 µm to 500 mm. It should be appreciated that the shape, number, size, spacing, etc. of the electrode sites may be selected according to an encephalic region to be sensed or stimulated.

In the embodiment according to the present disclosure, a surface of the electrode site that is exposed for contact with the brain tissue may also have a surface modification layer to improve an electrochemical property of the electrode site. As a non-limiting example, the surface modification layer may be obtained by using electropolymerization coating of PEDOT: PSS, sputtering an iridium oxide film, and the like, for decreasing impedance (such as electrochemical impedance at an operating frequency of 1 kHz) in the case where the flexible electrode acquires an electrical signal, and increasing a charge injection capability in the case where the flexible electrode applies electrical signal stimulation, thereby improving interaction efficiency. Specifically, surface modification may be performed by using any one or more of a conductive polymer and a conductive metal particle, wherein the conductive polymer may comprise Polydioxyethylthiophene, Poly (styrene sulfonate), polypyrrole, and the like, and a material of the conductive metal particle may comprise iridium, iridium oxide, platinum, platinum iridium alloy, and the like.

In the embodiment of the present disclosure, the flexible electrode may further include an additional wire layer, i.e. the flexible electrode in the present disclosure may include one or more wire layers. The additional wire layer may have a similar size, material, manufacturing method, etc. to the wire layer 303, which will not be detailed herein. When the flexible electrode includes an additional wire layer, these wire layers may be spaced apart by an additional insulating layer, and each wire layer includes a plurality of wires spaced apart from each other. The additional insulating layer may have a similar size, material, manufacturing method, etc. to the bottom insulating layer 301 and/or the top insulating layer 302, which will not be described in detail herein. When the flexible electrode does not include the separate electrode site layer, the electrode sites may be located in one or more of these additional wire layers and electrically coupled to wires in these wire layers. When the flexible electrode includes the separate electrode site layer, one or more wires in these additional wire layers may, through via holes in one or more of the bottom insulating layer, the top insulating layer, and the additional insulating layer, be electrically coupled to the electrode sites located below the bottom insulating layer or above the top insulating layer. By including a plurality of wire layers in the flexible electrode, the number and accuracy of signals transmitted by the flexible electrode can be increased in the case of a same sectional width, i.e., providing a high-accuracy and multi-channel electrode facilitates high-throughput interaction.

In the embodiment according to the present disclosure, the backend portion 340 of the flexible electrode 300 may include the backend site 306, which may be electrically coupled to one of the wires 305 and exposed to an outer surface of the flexible electrode through a via hole in at least one of the bottom insulating layer 301 or the top insulating layer 302, thereby enabling bidirectional signal transmission between the electrode site electrically coupled with the wire and a backend circuit when the backend portion 340 is connected to the backend circuit. In the embodiment according to the present disclosure, the backend site 306 may be located in the wire layer 303, as shown in FIG. 3. The backend circuit here may refer to a circuit at a backend of the flexible electrode, such as a signal recording circuit, a signal processing circuit, a signal generating circuit, or the like associated with the signal of the flexible electrode. In the embodiment according to the present disclosure, the flexible electrode may be coupled to the backend circuit in a connection manner, specifically, a ball gate array (BGA) package site as a backend site may be transferred to a commercial signal recording system by a printed circuit board (PCB), a flexible printed circuit (FPC), and the like, the connection manner including a ball placement patch and an anisotropic conductive film bonding (ACF Bonding), or the like. In the embodiment according to the present disclosure, the flexible electrode may also be integrated with the backend circuit, specifically, preprocessing functions such as signal amplification and filtering may be integrated on a dedicated chip, and then the chip is connected and packaged with an integrated PCB at a backend of the flexible electrode by means of bonding or the like, thereby enabling wireless transmission, charging, and the like. In this case, it is possible to use an independent flexible electrode and an independent dedicated chip as a backend circuit, to perform electrical connection between the flexible electrode and the dedicated chip by means of the ball placement patch or ACF Bonding; and it is also possible to reserve a certain space on a pre-taped-out wafer of a chip as a backend circuit, and directly manufacture the electrode on this basis, thereby enabling joint or separate processing of the chip and the electrode for higher integration.

In the embodiment according to the present disclosure, the backend site may not be located in the wire layer, i.e. the flexible electrode may include a separate backend site layer (not shown). Specifically, the backend site layer may be located between at least one of the top insulating layer or the bottom insulating layer and the wire layer and exposed through a via hole in the at least one of the top insulating layer or the bottom insulating layer. When the flexible electrode includes the separate backend site layer, the backend site may include a plurality of sub-layers in a thickness direction, wherein, a material of an adhesion sub-layer in the plurality of sub-layers that is close to the wire layer may be a material that can enhance adhesion between the electrode site and the wire, a material of a soldering flux layer in the middle of the plurality of sub-layers may be a soldering flux material, a material of a conductive sub-layer in the plurality of layers, like the wire layer described above, may be another metallic or non-metallic material with conductivity, and an outermost layer in the plurality of layers that may be exposed through one of the insulating layers is a protection sub-layer for anti-oxidation. As a non-limiting example, the backend site layer may be a metal film including three stacked sub-layers, wherein a first sub-layer close to the wire layer may be an adhesion sub-layer of nanometers to improve adhesion between the backend site layer and the wire layer, a second sub-layer as a soldering flux layer may be nickel (Ni), Pt, or palladium (Pd), and a third sub-layer as a conductive sub-layer may be Au, Pt, Ir, W, Mg, Mo, platinum iridium alloy, titanium alloy, graphite, carbon nanotube, PEDOT, or the like. It should be understood that the backend site layer may be made of another metallic or non-metallic material with conductivity. The backend site layer is taken as a portion connected with the backend processing system or chip, and a size, spacing, shape and the like of the sites thereof can be designed according to different connections to the backend. The backend site may have a planar size in micrometers and a thickness in nanometers. As a non-limiting example, the backend site may be a BGA package site with a diameter of 50 μm to 2000 μm, or a site in a shape of a circle, ellipse, rectangle, rounded rectangle, or chamfered rectangle with a side length of 50 μm to 2000 μm, and the backend site may have a thickness of 5 nm to 200 μm. It should be understood that the shape, size, etc. of the backend site are not limited to the ranges listed above, but may be changed according to design requirements.

In the embodiment according to the present disclosure, the flexible electrode 300 may further include a flexible separation layer (not shown). The flexible separation layer may be located at a lowermost layer of the entire flexible electrode, but it should be understood that the position of the flexible separation layer is not limited thereto, and one or more flexible separation layers located at different positions may be included in the flexible electrode. Preferably, the flexible separation layer may be manufactured between a substrate and the bottom insulating layer. A material that can be removed by a specific substance (such as a solution) may be used for the flexible separation layer, to separate two portions of the flexible electrode above and below the flexible separation layer while avoiding damage to the flexible electrode. Specifically, the flexible separation layer can be used for separating the entire electrode or only a flexible portion of the electrode from the substrate, separating a flexible substrate from a hard substrate, separating those portions that have an excessively strong adhesion force therebetween and need to be separated, or the like. In the embodiment of the present disclosure, the material of the flexible separation layer may be a metallic or non-metallic material, such as Ni, Cr, and aluminum (Al).

Figure 4:
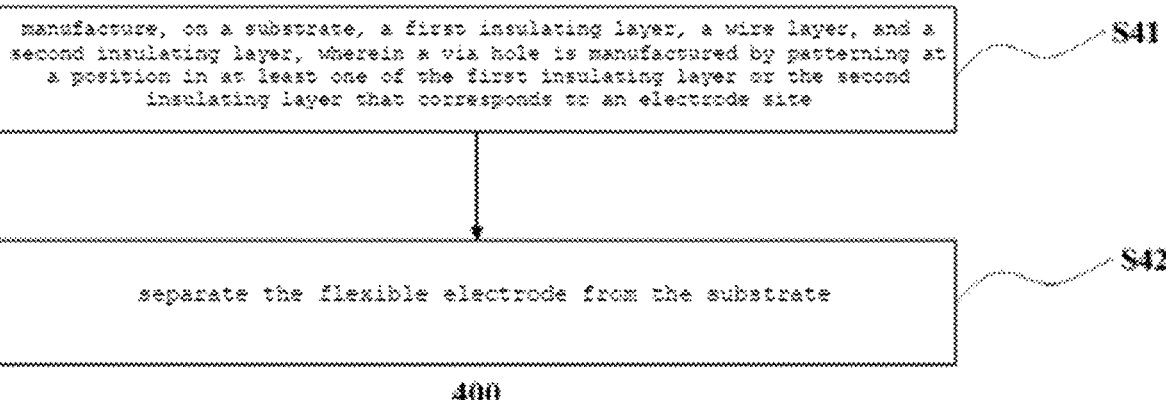
FIG. 4 illustrates a flow diagram of a method for manufacturing a flexible electrode for a brain according to an embodiment of the present disclosure.

FIG. 4 illustrates a flow diagram of a method 400 for manufacturing a flexible electrode according to an embodiment of the present disclosure. In the present disclosure, it is possible to manufacture a flexible electrode in nanometers by adopting a manufacturing method based on a micro-electro mechanical system (MEMS) process. As shown in FIG. 4, the method 400 may comprise: at S41, manufacturing, on a substrate, a first insulating layer, a wire layer, and a second insulating layer, wherein a via hole is manufactured by patterning, at a position in at least one of the first insulating layer or the second insulating layer that corresponds to an electrode site; and at S42, separating the flexible electrode from the substrate. The step of manufacturing the layers of the flexible electrode at S41 is detailed below in conjunction with FIG. 5.

Figure 5:
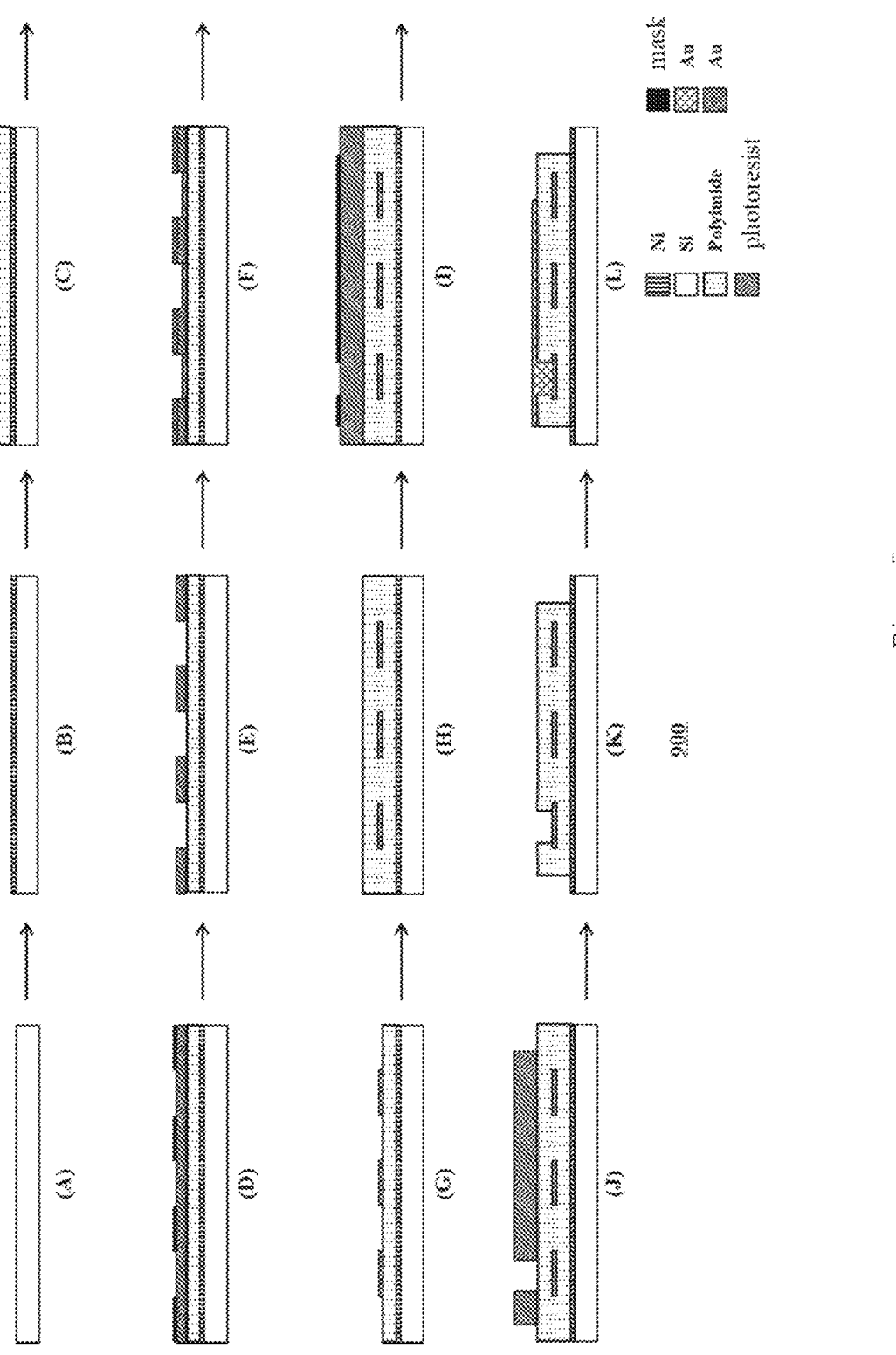
FIG. 5 illustrates a schematic view of a method for manufacturing a flexible electrode for a brain according to an embodiment of the present disclosure.

FIG. 5 illustrates a schematic view of a method 500 for manufacturing a flexible electrode according to an embodiment of the present disclosure. A manufacturing process and structure of a flexible separation layer, bottom insulating layer, wire layer, top insulating layer, electrode site layer, and other portions of the flexible electrode will be described in more detail in conjunction with FIG. 5.

View (A) of FIG. 5 illustrates a substrate of the electrode. In the embodiment according to the present disclosure, a hard substrate such as glass, quartz, and a silicon wafer, may be used. In the embodiment of the present disclosure, another soft material may be used as the substrate, such as a material the same as the material of the insulating layer.

View (B) of FIG. 5 illustrates the step of manufacturing the flexible separation layer on the substrate. The flexible separation layer may be removed by applying a specific substance, thereby facilitating separation of a flexible portion of the electrode from the hard substrate. In the embodiment shown in FIG. 5, Ni is taken as a material of the flexible separation layer, and another material such as Cr and Al may be used. In the embodiment according to the present disclosure, when the flexible separation layer is manufactured on the substrate by evaporation, an exposed portion of the substrate may be etched first, thereby improving flatness of the entire substrate after the evaporation. It should be appreciated that the flexible separation layer is an optional rather than necessary portion of the flexible electrode. According to a property of the selected material, the flexible electrode can also be easily separated without the flexible separation layer. In the embodiment according to the present disclosure, the flexible separation layer may also have a mark thereon, which may be used for alignment of subsequent layers.

View (C) of FIG. 5 illustrates manufacturing the bottom insulating layer on the flexible separation layer. As a non-limiting example, when a polyimide material is taken for the insulating layer, the manufacturing of the bottom insulating layer may include steps such as a film formation process, film formation curing, and reinforced curing to manufacture a film as the insulating layer. The film formation process may include coating polyimide on the flexible separation layer. The film formation curing may include a step-wise temperature increase to a higher temperature and heat preservation for film formation, thereby performing subsequent processing steps. The reinforced curing may include a multi-gradient temperature increase, preferably in the presence of a vacuum or nitrogen atmosphere, and several hours of baking, before the subsequent layers are manufactured. It should be understood that the above manufacturing process is merely a non-limiting example of the manufacturing process for the bottom insulating layer, and one or more steps thereof may be omitted, or more other steps may be included.

It should be noted that the above manufacturing process is aimed at an embodiment in which a bottom insulating layer in a flexible electrode without a bottom electrode site layer is manufactured and there is no via hole corresponding to an electrode site and a backend site in the bottom insulating layer. If the flexible electrode includes a bottom electrode site layer, the bottom electrode site layer may be manufactured on the flexible separation layer before the bottom insulating layer is manufactured. For example, Au and Ti may be sequentially evaporated on the flexible separation layer. A patterning step of a bottom electrode site will be detailed in the following description of a top electrode site. Accordingly, when the flexible electrode includes a bottom electrode site, in the process of manufacturing the bottom insulating layer, in addition to the above steps, the patterning step may be further included, for etching a via hole at a position in the bottom insulating layer that corresponds to the bottom electrode site. A patterning step of the insulating layer will be detailed in the following description of the top insulating layer.

Views (D) to (G) of FIG. 5 illustrate manufacturing the wire layer on the bottom insulating layer. As shown in view (D), photoresist and a mask may be applied on the bottom insulating layer. It should be understood that a patterned film may be prepared using lithography means, such as laser direct writing and e-beam lithography. In the embodiment according to the present disclosure, for a metal film such as the wire layer, a double layer of photoresist may be applied to facilitate manufacturing (evaporation or sputtering) and lift-off of the patterned film. By setting a pattern of the mask related to the wire layer, for example, the foregoing pattern of the wire layer, such as the pattern of the wire layer 303 of FIG. 3, can be implemented. Next, exposure and development may be performed to obtain a structure as shown in view (E). In the embodiment according to the present disclosure, for the exposure, contact lithography may be used, where the mask and the structure are exposed in a vacuum contact mode. In the embodiment according to the present disclosure, for patterns in different sizes, different developers and concentrations thereof may be used. In this step, layer-to-layer alignment may also be included. Next, film formation may be performed on the structure shown in view (E), for example, by using processes such as evaporation and sputtering, to deposit a metal film material such as Au, to obtain a structure shown in view (F). Next, lift-off may be performed to separate, by removing photoresist in a non-patterned region, a film in the non-patterned region and a film in a patterned region, to obtain a structure as shown in view (G), i.e., the wire layer manufactured.

In the embodiment according to the present disclosure, when the flexible electrode includes a separate backend site layer, the backend site layer may also be manufactured before the wire layer is manufactured. As a non-limiting example, the manufacturing process of the backend site layer may be similar to the manufacturing process of the metal film in the foregoing description of the wire layer.

Views (H) to (K) of FIG. 5 illustrate manufacturing the top insulating layer. For a photosensitive film, generally, patterning can be directly implemented by patterning exposure and development, but for a non-photosensitive material used by the insulating layer, patterning cannot be implemented by exposing and developing the material itself, so that it is possible to manufacture, on this layer, a sufficiently thick patterned anti-etching layer, then remove, by dry etching, a film in an area not covered by the anti-etching layer (meanwhile, the anti-etching layer is also thinned, so that there is a need to ensure that the anti-etching layer is thick enough), and then remove the anti-etching layer to pattern the non-photosensitive layer. As a non-limiting example, for the manufacturing of the insulating layer, photoresist may be used as the anti-etching layer. The manufacturing of the top insulating layer may include steps such as a film formation process, film formation curing, patterning, and reinforced curing, wherein view (H) illustrates a structure obtained after the film formation of the top insulating layer, view (I) illustrates applying photoresist and a mask on the top insulating layer after the film formation, view (J) illustrates a structure including the anti-etching layer obtained after the exposure and development, and view (K) illustrates a structure including the manufactured top insulating layer. The film formation process, film formation curing, and reinforced curing have been detailed in foregoing description of the bottom insulating layer, and are omitted here for the sake of brevity. The patterning step can be performed after the film formation curing, or after the reinforced curing, so that after the reinforced curing, the insulating layer has stronger anti-etching capability. Specifically, in the view (I), a layer of sufficiently thick photoresist is manufactured on the insulating layer by steps of spin-on PR coating, baking and the like. By setting a pattern of the mask related to the top insulating layer, it is possible to implement, for example, the pattern of the top insulating layer 302 shown in FIG. 3, i.e., contours of the cortical attachment portion 310, deep implantation portion 320, connection portion 330, and backend portion 340 of the flexible electrode 300, and a contour of the via hole implemented at the position in the top insulating layer 302 that corresponds to the electrode site and the backend site. In view (J), the pattern is transferred to the photoresist on the insulating layer by steps such as exposure and development to obtain the anti-etching layer, wherein a portion to be removed from the top insulating layer is exposed. It is possible to remove the exposed portion of the top insulating layer by oxygen plasma etching, and after flood exposure, remove photoresist remaining on the top insulating layer by using a developer or acetone, etc., to obtain a structure shown in view (K).

In the embodiment according to the present disclosure, before manufacturing the top insulating layer, it may be further tackified, to improve a bonding force between the bottom insulating layer and the top insulating layer.

When the flexible electrode includes a top electrode site layer, the method may further comprise manufacturing the top electrode site layer on the top insulating layer in the structure shown in view (K).

Figure 6:
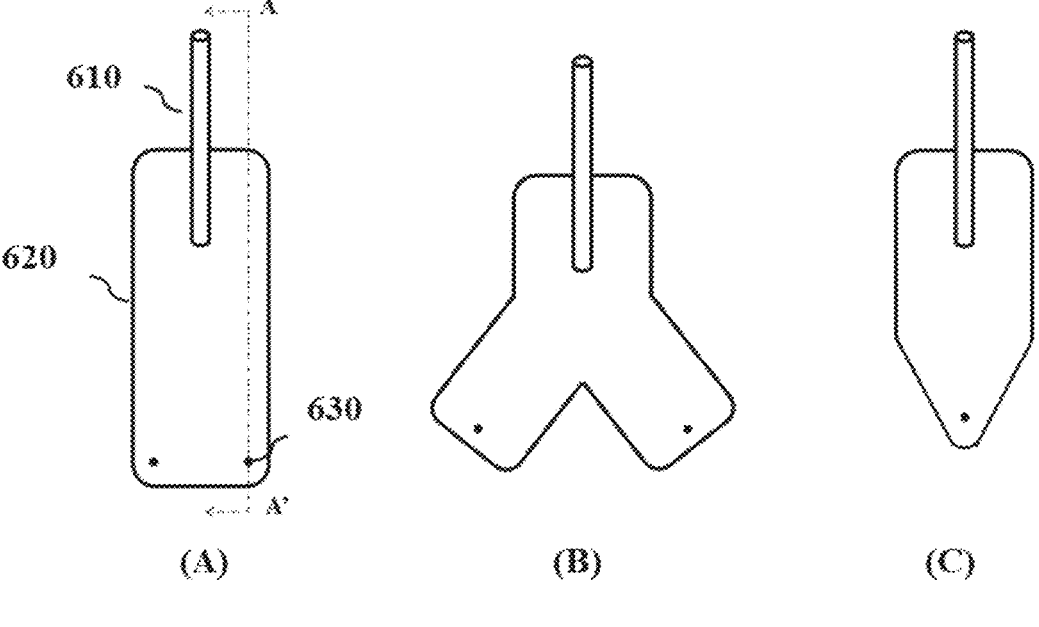
FIGS. 6 to 8 illustrate one non-limiting embodiment of a support bracket for a flexible electrode for a brain.
Figure 7:
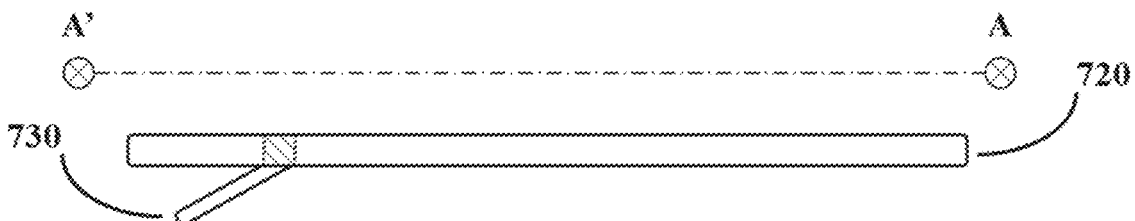
Figure 8:
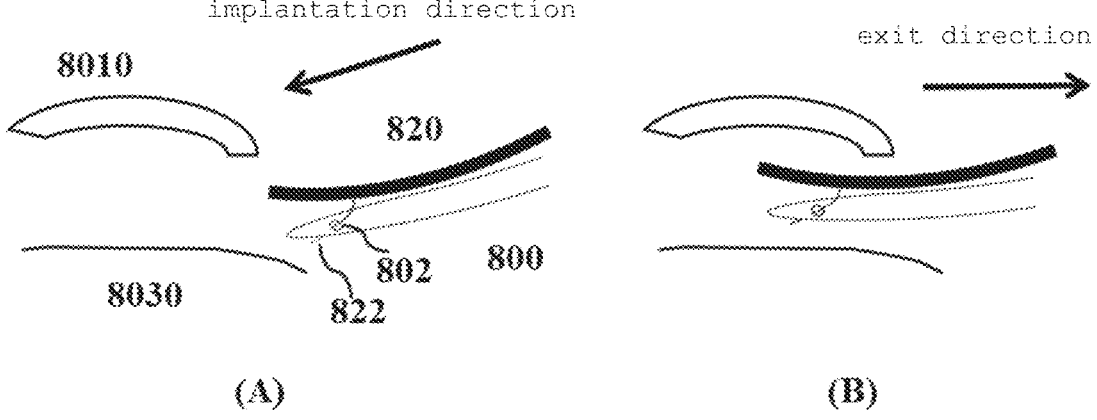

FIGS. 6 to 8 illustrate one non-limiting embodiment of a support bracket for a flexible electrode for a brain. FIG. 6 illustrates several different shapes of a support bracket, which mainly comprises a hard handle 610, a support bracket body 620 and an electrode hook 630, taking view (A) of FIG. 6 as an example. A size of the support bracket is flexibly defined depending on a specific size, shape and angle of the implanted electrode, and a placement angle thereof with respect to an encephalic region to reduce implantation difficulty. The support bracket body 620 has a certain flexibility, so that it can be bent to some extent to adapt to an uneven surgical region in surgical implantation, and has various forms such as a rectangle-like shape in view (A) of FIG. 6 or a Y-shape in view (B) of FIG. 6, or has a small and round head in view (C) of FIG. 6, to prevent scratching of a brain surface. The electrode hook 630 is used for hooking a mounting hole (e.g., the mounting hole in the cortical attachment portion, with a size of about 50 μm to 1 mm) on the flexible electrode to be implanted, and the electrode hook 630 may be made of metal such as a tungsten wire or degradable polymer such as PI and polylactic acid, and may be one or more in number. A section A-A' of the electrode hook 630 in view (A) is shown in FIG. 7, where 720 is the support bracket body, 730 is the electrode hook, and a shadow corresponds to an electrode hook positioning point in FIG. 6, wherein, a front of the electrode hook 730 does not exceed a foremost end of the support bracket body 720. It should be noted that the relationships in size and shape in FIG. 7 are schematic, and in practical applications, support brackets in different sizes and shapes can be designed according to requirements.

A material of the support bracket may include, but is not limited to: metal such as tungsten, platinum, titanium, and magnesium, and alloy thereof, a polymer material such as polyimide, polydimethylsiloxane (PDMS), hydrogel, epoxy, and polyethylene, and an inorganic or organic material such as chitosan and polyethylene glycol (PEG), which can be electrolyzed, hydrolyzed, pyrolyzed, and biodegraded. Therefore, the support bracket and/or decomposition products thereof do not generate toxicity to an organism, which can avoid damage to a surgical region where the electrode is implanted.

A mechanical structure for the support bracket may include, but not limited to a cantilever beam, a latch, a linkage mechanism, etc. and implantation is made using microfluidics, which allows that when implanted, the electrode is kept in a state of, including, but not limited to, flattened, rolled, wrapped, etc., after implanted and when retained in the brain, it is flattened and fits into the cerebral cortex, and it can be removed from the brain in a state of, including, but not limited to, flattened, rolled, wrapped, etc.

FIG. 8 illustrates a schematic diagram of a step of implanting a flexible electrode for a brain via a support bracket. As shown in view (A) of FIG. 8, the support bracket 820 carries the flexible electrode 800 for implantation into an encephalic region, and specifically, an electrode hook 822 on the support bracket 820 passes through a mounting hole 802 on the flexible electrode 800, so that the electrode 800 enters between a skull 8010 and a brain surface 8030 in an implantation direction indicated by an arrow in view (A) in a flattened state. Subsequently, as shown in view (B) of FIG. 8, when the flexible electrode 800 reaches a designated position of the brain surface 8030, the support bracket 802 is taken out in an exit direction indicated by an arrow in view (B), thereby completing the implantation of the flexible electrode 800.

Figure 9:
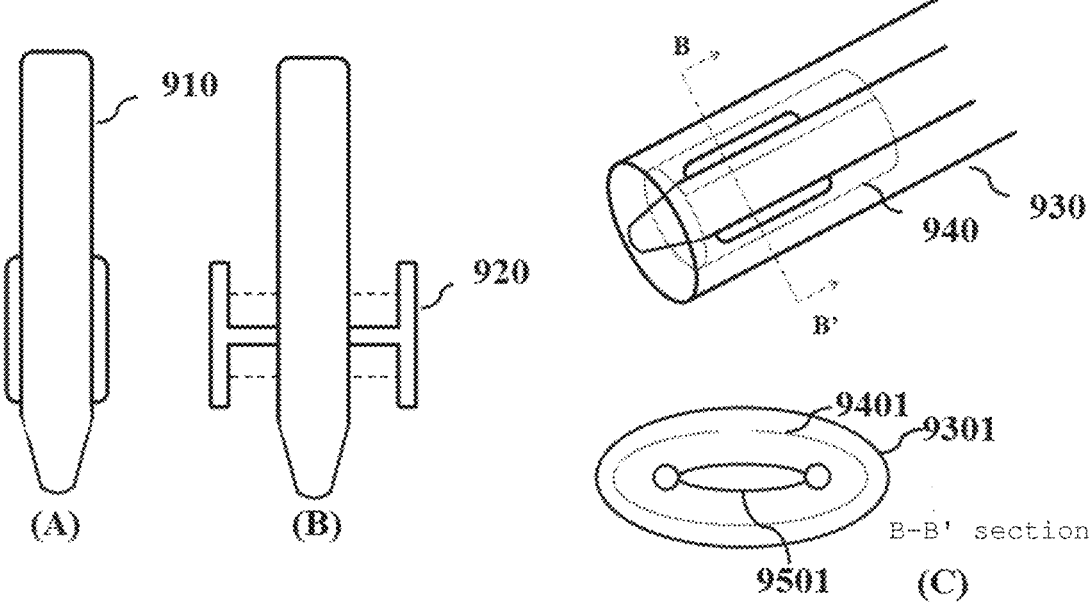
FIGS. 9 to 10 illustrate another non-limiting embodiment of a support bracket for a flexible electrode for a brain.
Figure 10:
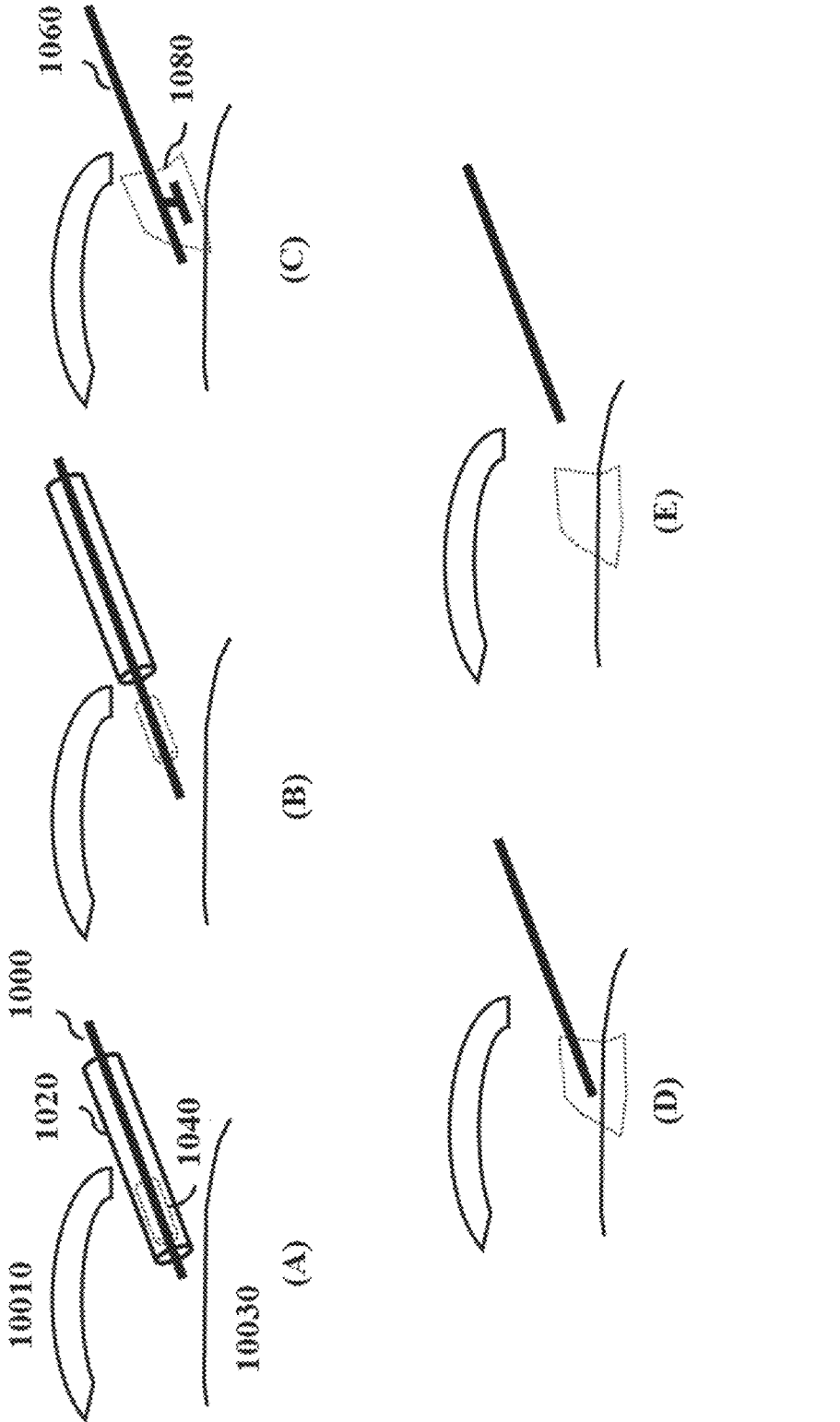

FIGS. 9 to 10 illustrate another non-limiting embodiment of a support bracket for a flexible electrode for a brain. Views (A) and (B) of FIG. 9 illustrate one shape of the support bracket, including a flat cylindrical support bracket body 910 and a flattening shelf 920 that can be unfolded. In particular, the flattening shelf 920 may be converted from a folded state in view (A) to an unfolded state in view (B) by a mechanical device such as pneumatic pressure and a linkage, or other implementations. View (C) of FIG. 9 illustrates one form of the flexible electrode ready for implantation, wherein an upper half of view (C) is a simplified perspective view of the electrode mounted on the support bracket and a lower half is a schematic view of a B-B' section of the perspective view. It should be noted that the form of the electrode is simplified into a relatively standard flat cylinder in view (C), and in fact, the fit between the flexible electrode and the support bracket can be designed into any shape as needed, such as a portion at a front end that is approximate to a frustum cone. As shown in the figure, 930 which is a tube for protecting the flexible electrode and 940 which is the flexible electrode wrapped around the support bracket are embodied on the B-B' section, as a tube 9301 wrapped outwards, and a flexible electrode 9401 wrapped around a support bracket 9501 in a rolled state, respectively.

FIG. 10 is a schematic view of a step of implanting a flexible electrode for a brain via a support bracket according to the foregoing embodiment. As shown in view (A) of FIG. 10, a support bracket in a folded form 1020 is thereon wrapped with a flexible electrodes 1000 and implanted between a skull 10010 and a brain surface 10030 under protection of a tube 1040. When the support bracket, with the flexible electrode 1000 carried, reaches a designated position, the tube 1040 is drawn out, as shown in view (B) of FIG. 10. Subsequently, as shown in view (C) of FIG. 10, the support bracket is opened into a support bracket in a flattening shelf form 1060, and the flexible electrode 1000 is flattened from a rolled state to the flexible electrode in a flattened state 1080 by means of the flattening shelf. Next, as shown in view (D) of FIG. 10, the flattening shelf is folded up so that the support bracket is restored to the folded form 1020. Finally, the support bracket is drawn out as shown in view (E) of FIG. 10 to complete the flattening and implantation of the flexible electrode.

Figure 11:
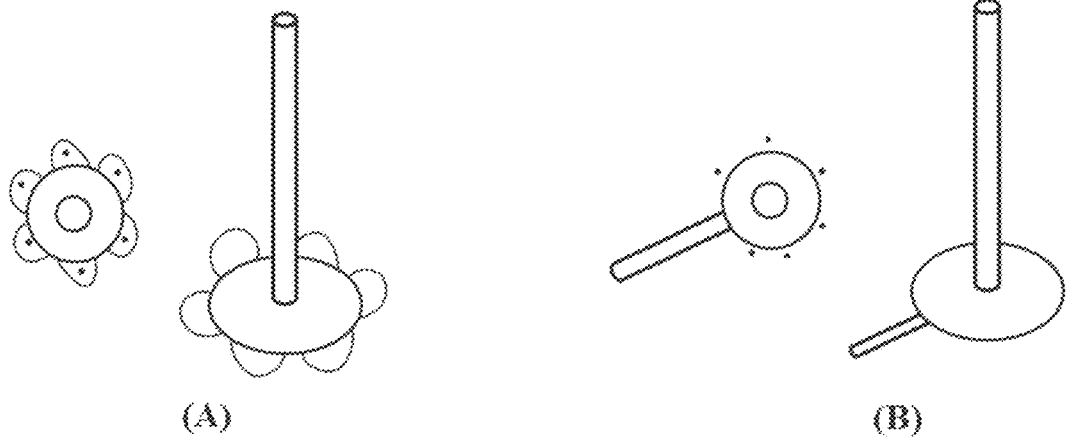
FIGS. 11 to 12 illustrate yet another non-limiting embodiment of a support bracket for a flexible electrode for a brain.
Figure 12:
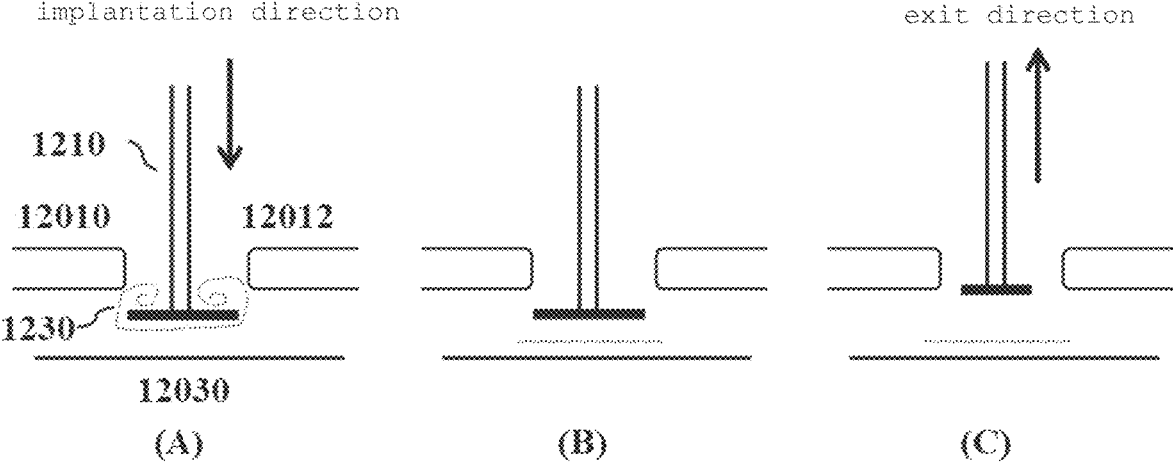

FIGS. 11 to 12 illustrate yet another non-limiting embodiment of a support bracket for a flexible electrode for a brain. View (A) of FIG. 11 illustrates one shape of the support bracket, where a hard handle and a flower-like support bracket body are included, the support bracket being shown in view (B) of FIG. 11 when unfolded. In particular, the support bracket may be unfolded by a mechanical device such as pneumatic pressure, a linkage, or other implementations. FIG. 12 is a schematic view of a step of implanting a flexible electrode for a brain via a support bracket according to the foregoing embodiment. As shown in view (A) of FIG. 12, the support bracket 1210 carries the flexible electrode 1230 wrapped on the support bracket 1210 and is implanted between a skull and a brain surface 12030 from a gap between skulls 12010 and 12012. The support bracket 1210 delivers the flexible electrode 1230 in a rolled state in an implantation direction indicated by an arrow in view (A) of FIG. 12 to a designated position, and then the support bracket 1210 is unfolded, as shown in view (B) of FIG. 12, such that the flexible electrode 1230 is flattened between the skull 12010/12012 and the brain surface 12030. Then, the support bracket 1210 is changed into a folded state and drawn out in an exit direction as indicated by an arrow in view (C) of FIG. 12, thereby completing the flattening and implantation of the electrode.

In the present disclosure, there is provided a flexible electrode for a brain and a method for manufacturing same. A flexible material is used for the flexible electrode in place of a hard silicon-based electrode, a conductive material is wrapped by using polymer as an insulating layer, and a thickness of the electrode is reduced, to reduce bending rigidity thereof, thereby improving mechanical performance mismatch between the electrode and tissue, and finally providing a long-term stable electric signal sense and stimulation interface. The flexible electrode has much higher selectivity and channel number than a conventional brain electrode, with the characteristic of less trauma, so that it is suitable for use in some minimally invasive scenes to implement good sense and stimulation functions for brain signals. Moreover, the flexible electrode can synchronously record and stimulate surface and deep neural electrical signals of the cerebral cortex, which is of great significance for understanding complex neural responses and analyzing relationships between neural signals of different encephalic regions.

The terms "front", "back", "top", "bottom", "above", "below", and the like in the description and claims, if any, are used for descriptive purposes and not necessarily for describing permanent relative positions. It should be understood that the terms so used are interchangeable where appropriate such that the embodiments of the present disclosure described herein are, for example, capable of operating in other orientations different from those shown herein or otherwise described.

As used herein, the term "exemplary" means "serving as an example, instance, or illustration", and not as a "model" that is to be reproduced exactly. Any implementation exemplarily described herein is not necessarily to be construed as preferred or advantageous over other implementations. Moreover, the present disclosure is not limited by any expressed or implied theory presented in the above TECH-NICAL FIELD, BACKGROUND, SUMMARY, OR DETAILED DESCRIPTION As used herein, the term "substantially" means encompassing any minor variations caused by imperfections in design or manufacturing, tolerances of devices or components, environmental effects and/or other factors. The term "substantially" also allows for differences from a perfect or ideal situation caused by parasitic effect, noise, and other practical considerations that may exist in a practical implementation.

For reference purposes only, similar terms such as "first" and "second" can be used herein, and thus are not intended to be limiting. For example, unless clearly indicated by the context, the terms "first", "second" and other such numerical terms involving structures or elements do not imply a sequence or order It should be further understood that the term "comprise/include", when used herein, specifies the presence of stated features, entireties, steps, operations, units, and/or components, but do not preclude the presence or addition of one or more other features, entireties, steps, operations, units, components, and/or combinations thereof.

As used herein, the term "and/or" includes any and all combinations of one or more of listed items in association. Terms used herein are for the purpose of describing specific embodiments only and are not intended to limit the present disclosure. As used herein, singular forms "a", "an", and "the" are also intended to include plural forms, unless clearly indicated by the context otherwise.

Those skilled in the art should realize that boundaries between the above operations are merely illustrative. Multiple operations can be combined into a single operation, the single operation can be distributed in additional operations, and the execution of the operations can be at least partially overlapped in time. Moreover, an alternative embodiment can include multiple instances of specific operations, and the order of the operations may be altered in various other embodiments. However, other modifications, variations, and alternatives are also possible. Accordingly, the description and the accompanying drawings should be regarded as illustrative rather than restrictive.

Although some specific embodiments of the present disclosure have been described in detail by means of examples, it should be understood by those skilled in the art that the above examples are for illustration only and are not intended to limit the scope of the present disclosure. The embodiments disclosed herein can be combined arbitrarily without departing from the spirit and scope of the present disclosure. Those skilled in the art should also appreciate that various modifications can be made to the embodiments without departing from the scope and spirit of the present disclosure. The scope of the present disclosure is defined by the appended claims.

What is claimed is:

1. A flexible electrode for a brain, comprising:
a cortical attachment portion capable of being implanted into the brain; and
one or more deep implantation portions;
    wherein the cortical attachment portion has a sheet-like structure capable of covering and being flattened to fit against at least a portion of a cerebral cortex after an implantation;
    wherein the one or more deep implantation portions being configured to be implanted into a deep region of the brain and bent relative to the cortical attachment portion after the implantation;
    wherein the flexible electrode comprises:
        a first insulating layer,
        a second insulating layer, and
        a wire layer located between the first insulating layer and the second insulating layer; and
    wherein at least one of the one or more deep implantation portions and the cortical attachment portion, each comprises one or more electrode sites, each of which is electrically coupled to at least one wire in the wire layer and in contact with the brain after the flexible electrode is implanted into the brain, to acquire, from the brain, at least one first electrical signal and transmit the at least one first acquired electrical signal by the at least one wire, or apply, to the brain, at least one second electrical signal received by the at least one wire;
    wherein the wire layer comprises a conductive sub-layer;
    wherein a material of the conductive sub-layer is any one of gold, platinum, iridium, tungsten, platinum iridium alloy, titanium alloy, graphite, carbon nanotube, PEDOT, or any combination thereof; and
    wherein the conductive sub-layer has a thickness of 5 nanometers to 200 micrometers, or, when neither at least one electrode site nor at least one backend site is located in the wire layer, the wire layer further comprises an adhesion sub-layer close to either the at least one electrode site or the at least one backend site, and a material of the adhesion sub-layer is any one of chromium, tantalum, tantalum nitride, titanium, titanium nitride, or any combination thereof.

2. The flexible electrode according to claim 1, wherein at least one deep implantation portion of the one or more deep implantation portions extends from the cortical attachment portion, and has at least one mounting through-hole, through which an electrode implantation device is attached to the at least one deep implantation portion for the implantation of the at least one deep implantation portion.

3. The flexible electrode according to claim 1, wherein, the flexible electrode comprises a plurality of wire layers which are spaced apart by an additional insulating layer, and each of the wire layers comprises therein a plurality of wires spaced apart from each other.

4. The flexible electrode according to claim 1, wherein, the flexible electrode is configured to be implanted into the brain using a support bracket.

5. The flexible electrode according to claim 4, wherein, the support bracket has a micromechanical mechanism, comprising a cantilever beam, a latch, or a linkage mechanism.

6. The flexible electrode according to claim 4, wherein, the support bracket is configured to implant the flexible electrode by microfluidics.

7. The flexible electrode according to claim 4, wherein, a material of the support bracket is any one of tungsten, platinum, titanium, magnesium, polyimide, polydimethylsiloxane, hydrogel, epoxy, polyethylene, chitosan, polyethylene glycol, or any combination thereof.

8. The flexible electrode according to claim 4, wherein, the support bracket is configured to implant the cortical attachment portion and the at least one deep implantation portion of the flexible electrode into a portion of the brain that is not easily accessible by craniotomy, the portion being located at one or more of a frontal lobe, occipital lobe, temporal lobe, or central cerebral great vessel.

9. The flexible electrode according to claim 4, wherein, the support bracket is configured to implant the flexible electrode along a gap between the brain and a skull.

10. The flexible electrode according to claim 1, wherein the flexible electrode is configured to remain in a flattened, rolled, or wrapped state during the implantation, and is capable of being removed from the brain in the flattened, rolled, or wrapped state.

11. The flexible electrode according to claim 1, wherein, at least one electrode site of the one or more electrode sites is located in the wire layer and exposed through at least one via hole in at least one of the first insulating layer or the second insulating layer.

12. The flexible electrode according to claim 1, wherein at least one electrode site of the one or more electrode sites is located on an outer side of at least one of the first insulating layer or the second insulating layer, and electrically coupled to a wire in the wire layer through at least one via hole in the at least one layer.

13. The flexible electrode according to claim 12, wherein, the at least one electrode site comprises a conductive sub-layer, and a material of the conductive sub-layer is any one of gold, platinum, iridium, tungsten, magnesium, molybdenum, platinum iridium alloy, titanium alloy, graphite, carbon nanotube, PEDOT, or any combination thereof.

14. The flexible electrode according to claim 13, wherein, the at least one electrode site further comprises an adhesion sub-layer close to the wire layer, the adhesion sub-layer being made of a material capable of enhancing adhesion between the electrode site and the wire layer.

15. The flexible electrode according to claim 1, wherein a maximum side length or diameter of the one or more electrode sites is 1 micrometer to 500 micrometers, and a spacing between the one or more electrode sites is 10 micrometers to 10 millimeters therebetween.

16. The flexible electrode according to claim 15, wherein, at least one first electrode site of the at least one deep implantation portion has a smaller size than at least one second electrode site of the cortical attachment portion.

17. The flexible electrode according to claim 16, wherein, the at least one first electrode site of the at least one deep implantation portion has a maximum side length or diameter of 1 micrometer to 2 millimeters, and the at least one second electrode site of the cortical attachment portion has a maximum side length or diameter of 1 micrometer to 500 millimeters.

18. The flexible electrode according to claim 1, wherein, a surface of at least one electrode site of the one or more electrode sites that is in contact with a biological tissue has a surface modification layer that is configured to improve an electrochemical property of the at least one electrode site.

19. The flexible electrode according to claim 18, wherein, surface modification is performed by using any one or more of a conductive polymer and a conductive metal particle, the conductive polymer comprising Polydioxyethylthiophene, Poly (styrene sulfonate), polypyrrole, and a material of the conductive metal particle comprising iridium, iridium oxide, platinum, and platinum iridium alloy.

20. The flexible electrode according to claim 1, further comprising one or more backend portions extending from the cortical attachment portion, wherein at least one backend portion of the one or more backend portions comprises a backend site, which is coupled to one of the wires in the wire layer and a backend circuit, to implement bidirectional signal transmission between the electrode site electrically coupled to the one of the wires and the backend circuit.

21. The flexible electrode according to claim 20, wherein, the backend site is located in the wire layer and exposed through a through-hole in at least one of the first insulating layer or the second insulating layer.

22. The flexible electrode according to claim 20, wherein, the backend site is located between at least one of the first insulating layer or the second insulating layer and the wire layer, and exposed through a through-hole in the other of the first insulating layer and the second insulating layer.

23. The flexible electrode according to claim 22, wherein, the backend site comprises a conductive sub-layer, and a material of the conductive sub-layer is any one of gold, platinum, iridium, tungsten, magnesium, molybdenum, platinum iridium alloy, titanium alloy, graphite, carbon nanotube, PEDOT, or any combination thereof; or the backend site comprises an adhesion sub-layer close to the wire layer, and a material of the adhesion sub-layer being is any one of chromium, tantalum, tantalum nitride, titanium, and titanium nitride, or any combination thereof, or the backend site has a thickness of 5 nanometers to 200 micrometers.

24. The flexible electrode according to claim 1, wherein, the first insulating layer and the second insulating layer have a thickness of 100 nanometers to 300 micrometers, or a material of the first insulating layer and the second insulating layer is any one of polyimide, polydimethylsiloxane, parylene, epoxy, polyamide imide, SU-8 photoresist, silica gel, silicone rubber, or any combination thereof.

25. The flexible electrode according to claim 1, further comprising a flexible separation layer, wherein, the flexible separation layer is capable of being removed by a specific substance to separate a part of the flexible electrode without damage to the flexible electrode.

26. The flexible electrode according to claim 25, wherein, a material of the flexible separation layer is any one of nickel, chromium, and aluminum, or any combination thereof, or the flexible separation layer further comprises an adhesion sub-layer, and a material of the adhesion sub-layer is chromium, tantalum, tantalum nitride, titanium, or titanium nitride.

27. The flexible electrode according to claim 1, wherein, a material of the wire layer is any one of magnesium, molybdenum, molybdenum alloy, or any combination thereof, and a material of the first insulating layer and the second insulating layer is any one of polylactic acid, or polylactic acid-glycolic acid copolymer, or any combination thereof, so that the flexible electrode is biodegradable.

28. A method for manufacturing a flexible electrode for a brain, the flexible electrode being the flexible electrode according to claim 25, the method comprising:

manufacturing, on a substrate, the first insulating layer, the wire layer, the second insulating layer, and the electrode site; and separating the flexible electrode from the substrate, wherein the at least one via hole is manufactured by patterning, at a position of at least one of the first insulating layer or the second insulating layer that corresponds to the at least one electrode site.

\* \* \* \* \*